United States Patent [19]

Fuchs et al.

[11] Patent Number: 4,482,731

[45] Date of Patent: Nov. 13, 1984

[54] PROCESS FOR THE PREPARATION OF TRANS-3-(Z-2-CHLORO-2-ARYL-VINYL)-2,2-DIMETHYL-CYCLOPROPANE-1-CARBOXYLIC ACID DERIVATIVES, NEW INTERMEDIATE PRODUCTS FOR THIS PROCESS AND A PROCESS FOR THEIR PREPARATION AND THE USE OF INTERMEDIATE PRODUCTS IN AGENTS FOR

[75] Inventors: Rainer Fuchs; Wilhelm Stendel, both of Wuppertal, Fed. Rep. of Germany

[73] Assignee: Bayer Aktiengesellschaft, Leverkusen, Fed. Rep. of Germany

[21] Appl. No.: 297,479

[22] Filed: Aug. 28, 1981

[30] Foreign Application Priority Data

Sep. 18, 1980 [DE] Fed. Rep. of Germany ....... 3035149

[51] Int. Cl.$^3$ .............................................. C07C 69/76
[52] U.S. Cl. .................................. 560/08; 260/465 D; 260/544 D; 260/544 S; 568/308; 568/329; 562/405; 424/308; 424/315

[58] Field of Search ............................ 560/8; 562/405; 424/308, 315; 260/465 D, 544 D, 544 S

[56] References Cited

U.S. PATENT DOCUMENTS 4,388,322  6/1983  Fuchs .

FOREIGN PATENT DOCUMENTS 0033160  2/1980  European Pat. Off. ................ 560/8
2916417  4/1979  Fed. Rep. of Germany .......... 560/8

*Primary Examiner*—Paul J. Killos
*Attorney, Agent, or Firm*—Sprung, Horn, Kramer & Woods

[57] ABSTRACT

The invention relates to a process for preparing trans-3-(Z-2-chloro-2-(4-aryl)-vinyl)-2,2-dimethyl-cyclopropane-1-carboxylic acid derivatives of Formula (I) from corresponding dehalogenated compounds of Formula (II) by dehalogenation. The invention also includes to the novel compounds of Formula (III) and a halogenation process for their production. The compounds of the invention are useful as intermediates and/or insecticides or acaricides.

13 Claims, No Drawings

PROCESS FOR THE PREPARATION OF TRANS-3-(Z-2-CHLORO-2-ARYL-VINYL)-2,2-DIMETHYL-CYCLOPROPANE-1-CARBOXYLIC ACID DERIVATIVES, AND THE USE OF INTERMEDIATE PRODUCTS IN AGENTS FOR COMPATING PESTS

The invention relates to an unobvious process for the preparation of certain trans-3-(Z-2-chloro-2-aryl)-vinyl)-2,2-dimethyl-cyclopropane-1-carboxylic acid derivatives, to new intermediate products for this process and to a process for their preparation, and to the use of intermediate products as agents for combating pests, especially as insecticides and acaricides.

It has already been disclosed that mixtures of the (±)-cis and (±)-trans forms of 3-(E/Z-2-chloro-2-(4-chlorophenyl)-vinyl)-2,2-dimethyl-cyclopropane-1-carboxylic acid (±)-(α-cyano-4-fluoro-3-phenoxy-benzyl) ester have an insecticidal and acaricidal action (see DE-OS (German Published Specification) No. 2,730,515).

Furthermore, German Patent Application P.29 36 864 relates to diastereomer mixtures of Z- and E-trans-3-(2-chloro-2-(4-chloro-phenyl)-viny)-2,2-dimethyl-cyclo- propane-1-carboxylic acid (α-cyano-4-fluoro-3-phenoxy- benzyl) ester.

The above-mentioned patent application describes the resolution of E/Z-isomer mixtures into the E- and Z-diastereomers of trans-3-(2-chloro-2-(4-chloro-phenyl)-vinyl)-2,2-dimethyl-cyclopropane-1-cyclopropane-1-carboxylic acid by two extraction processes. However, these resolution processes are not very suitable for the resolution of relatively large amounts of substance because of the high expenditure on apparatus.

The present invention provides a process for the preparation of trans-3-(Z-2-chloro-2-(4-aryl)-vinyl)-2,2-dimethyl-cyclopropane-1-carboxylic acid derivatives of the formula

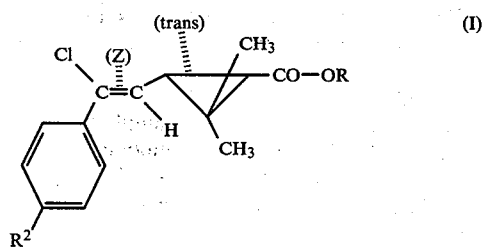

in which $R^2$ represents a hydrogen or chlorine atom and R represents a hydrogen atom, an alkali metal or one equivalent of an alkaline earth metal, an optionally substituted ammonium ion, an alkyl radical, or a phenoxy-benzyl radical which is optionally substituted by alkyl, alkenyl, alkinyl, halogen and/or cyano, characterised in that a trans -3-(1,2-dihalogen-2-chloro-2-(4-chloro-phenyl)-ethyl)-2,2-dimethyl-cyclopropane-1-carboxylic acid derivatives of the formula

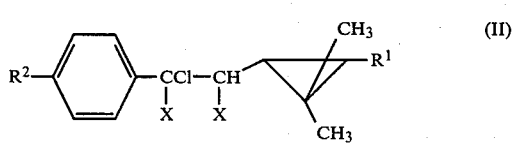

in which $R^2$ represents a hydrogen or chlorine atom, $R^1$ represents a cyano, acetyl, chlorocarbonyl or a —COOR radical, wherein R has the above-mentioned meaning, and X represents a chlorine or bromine atom, is reacted with a dehalogenating agent suitable for the elimination of two vicinal halogen atoms, if appropriate in the presence of a diluent, if appropriate at a temperature between 0° and 150° C., and, if $R^1$ in the compound of formula (II) does not denote the —COOR radical, the product of the formula

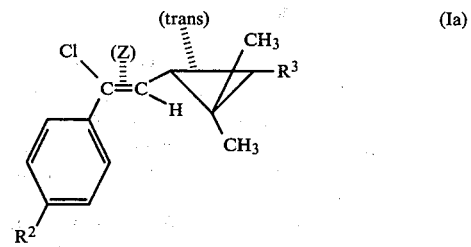

in which $R^2$ represents a hydrogen or chlorine atom and $R^3$ represents a cyano, acetyl or chlorocarbonyl radical, is converted into a compound of the formula (I); and, if desired, the product of formula (I) is converted into a compound of formula (I) in which R has one of its other alternative meanings.

As used herein and unless otherwise specifed, the terms "alkyl", "alkenyl" and "alkinyl" refers preferably to groups containing up to 8, especially up to 4 carbon atoms and the term "halogen" refers preferably to chlorine, bromine or fluorine, especially chlorine or fluorine and more specifically chlorine.

The present invention further provides as new compounds, the trans-3-(1,2,2-trichloro-2-aryl-ethyl)-2,2-dimethyl-cyclopropane-1-carboxylic acid derivatives of the formula

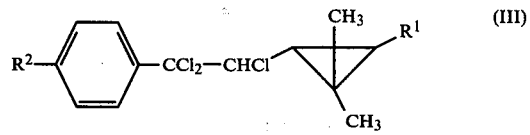

in which $R^1$ and $R^2$ have the meaning given above for the compounds of formula (II).

The invention further relates to a process for the production of compounds of the formula (III), characterised in that a trans -3-(E/Z-2-chloro-2-aryl-vinyl)-2,2-dimethyl-cyclopropane-1-carboxylic acid derivative of the formula

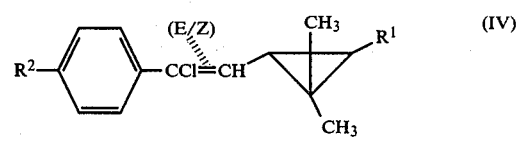

in which $R^1$ and $R^2$ have the meaning given above for the compounds of formula (II), is reacted with chlorine, if appropriate in the presence of a diluent, at a temperature between −50° and +50° C., and if $R^1$ in the compound of formula (IV) does not denote the —COOR radical, the products of the formula

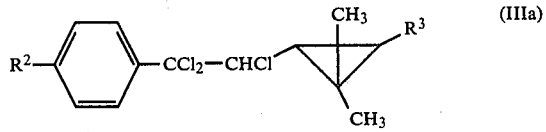

in which

R² represents a hydrogen or chlorine atom and

R³ represents a cyano, acetyl or chlorocarbonyl radical, is then converted, if desired, into a compound of the formula (III) in which R¹ represents —COOR.

The present invention furthermore relates to the use of compounds of the formula (III) in which R¹ represents a phenoxybenzyloxycarbonyl radical which is optionally substituted by alkyl, alkenyl, alkinyl, halogen and/or cyano, as active compound components in insecticidal and acaricidal agents, in particular in ectoparasiticides.

Surprisingly, the compounds of the formula (I) with the Z-configuration can be prepared in very good yields from E/Z-diastereomer mixtures of the compounds of the formula (IV) containing any proportion of the isomers with the E-configuration, by the process according to the invention, it being possible for the proportion of E-isomers to be reduced to less than 5%.

If, for example, trans-3-(1,2,2-trichloro-2-(4-chlorophenyl)-ethyl)-2,2-dimethyl-cyclopropane-1-carboxylic acid nitrile and zinc are used as starting substances, the course of the reaction in the process according to the invention for the preparation of compounds of the formula (I) is illustrated by the following equation:

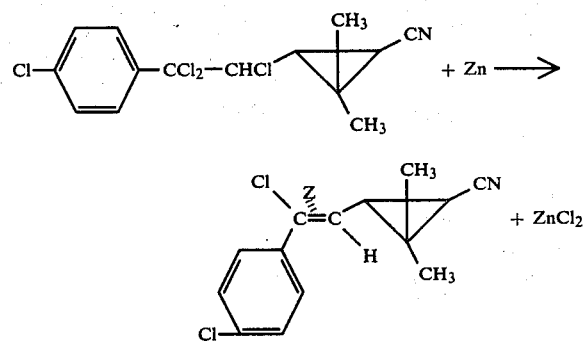

Dehalogenating agents which can be employed in the process according to the invention are described in the literature (see Houben-Wehy Methoden der organischen Chemie (Methods of Organic Chemistry), 4th edition (1972) Volume 5/1 b, pages 180–204, Thieme-Verlag, Stuttgart).

Suitable dehalogenating agents which may be mentioned are: (a) metals, such as sodium, potassium, magnesium, iron, nickel, copper zinc or alloys thereof; (b) alkali metal iodides or bromides, such as sodium iodide or bromide or potassium iodide or bromide; (c) reducing metal compounds, such as chromium-II sulphate and copper-I bromide, and (d) phosphorus-III compounds, such as triphenylphosphine and phosphorus acid tri-(dimethyl-amide).

Zinc is preferably used as the dehalogenating agent for the process according to the invention.

The process according to the invention for the preparation of compounds of the formula (I) is preferably carried out using diluents. These include, above all, in addition to water, organic solvents, in particular hydrocarbons (such as benzene, toluene or xylene), ethers (such as diethyl ether and dibutyl ether, glycol dimethyl ether, diglycol dimethyl ether, tetrahydrofuran and dioxane), ketones (such as acetone, methyl ethyl ketone, methyl isopropyl ketone and methyl isobutyl ketone), carboxylic acids and esters thereof (such as acetic acid and its methyl and ethyl ester), carboxylic acid amides (such as dimethylformamide and dimethylacetamide), and alcohols (such as methanol, ethanol, propanols and butanols).

The reaction temperature in the process for the preparation of compounds of the formula (I) is in general kept at a temperature between 0° and 150° C., preferably at a temperature between 20° and 120° C.

The process is carried out under normal pressure or slightly increased or reduced pressure, and in general between 0.1 and 10 bars.

For carrying out the process according to the invention, 1 to 2 moles, preferably 1 to 1.5 moles, of dehalogenating agent are employed per mole of starting compound of the formula (II). In a preferred embodiment, the dehalogenating agent is initially introduced into the reaction vessel in one of the above-mentioned diluents and the starting compound of the formula (II) is slowly added. The reaction mixture is then stirred, preferably at elevated temperature, until the reaction has ended.

Working up can be carried out by customary methods; for example, if the solvent is water-miscible, it is distilled off and the residue is shaken with water and an organic solvent which is virtually immiscible with water (such as methylene chloride). The organic phase is separated off, washed with water and dried. After distilling off the solvent, the products of the formula (I) remain as a solid or oily residue.

As already mentioned, compounds of the formula (I) or (Ia), or of the formula (III) or (IIIa), can by customary methods be "trans-functionalised", that is to say converted into other compounds of the formula (I) or (III), respectively before or after the process according to the invention, only the meanings of the functional groups R or R³, or R¹ or R³, respectively, being changed.

Such conversions are, for example (a) saponification of acid chlorides or cyano compounds of the formula (Ia) or (IIIa) (R³: —CO—Cl or —CN) to give the corresponding carboxylic acids, for example by heating with aqueous alkali metal hydroxide solutions; (b) esterification of acid chlorides of the formula (Ia) or (IIIa) (R³: —CO—Cl) by reaction with alcohols (such as for example alkanols and phenoxybenzyl alcohol) or by reaction with optionally substituted phenoxbenzaldehydes in the presence of water-solubule cyanides; (c) a haloform reaction of acetyl compounds of the formula (Ia) or (IIIa) (R³: —CO—CH₃) to give the corresponding carboxylic acids, for example a reaction with aqueous sodium hypochlorite solution; or (d) conversion of carboxylic acid derivatives of the formula (I) into compounds of formula (I), for example by saponification of the lower alkyl esters and reaction of the resulting carboxylic acids with thionyl chloride to give the corresponding acid chlorides, by customary methods.

Preferred trans-3-(1,2-dihalogen-2-chloro-2-arylethyl)-2,2-dimethyl-cyclopropane-1-carboxylic acid derivatives of formula (II) to be used as starting substances in the process according to the invention for the preparation of compounds of the formula (I), are those, in which R² represents a hydrogen or chlorine atom, and
R¹ represents a cyano, acetyl, chlorocarbonyl or —COOR radical, wherein R represents a hydrogen atom, a sodium, potassium, C₁ to C₄-alkyl or meta-phenoxy-benzyl radical which is optionally by cyano and/or fluorine substituted, and boxylic acid derivatives and α-chloro-4-chloro-benzylphosphonic acid dialkyl esters by a process described in the patent literature (see Published European Patent Application (Application No. 79 101,864.1)).

The present patent application also relates, as mentioned previously, to the pesticidal use of certain intermediate products of the formula (III), and preferably of trans-3-(1,2,2-trichloro-2-(4-chloro-phenyl)-ethyl)-2,2-dimethyl-cyclopropane-1-carboxylic acid phenoxybenzyl esters of the formula

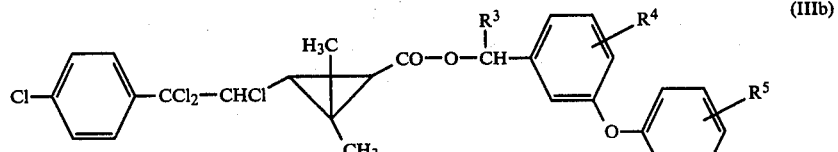

X has the above-mentioned meaning.

Particularly preferred starting substances are the new compounds of the formula (III) wherein R² represents a chlorine atom and
R¹ has the meaning given immediately above as preferred.

Examples of the compounds of the formula (III) which may be mentioned are: trans-3-(1,2,2-trichloro-2-(4-chloro-phenyl)-ethyl)-2,2-dimethyl-cyclopropane-1-carboxylic acid and its chloride, its sodium or potassium salt, its nitrile, its methyl, ethyl, n- or iso-propyl or n-, iso-, sec.- or tert.-butyl ester, its 3-phenoxy-benzyl ester, its α-cyano-3-phenoxy-benzyl ester, its 4-fluoro-3-phenoxy-benzyl ester or its α-cyano-4-fluoro-3-phenoxy-benzyl ester, and trans-3-(1,2,2-trichloro-2-(4-chloro-phenyl)-ethyl)-2,2-dimethyl-1-cyclopropyl) methyl ketone.

The starting compounds of the formula (II) - this formula also includes the new compounds of the formula (III) - are obtained in a manner which is in itself known, by reaction of trans-3-(E/Z-2-chloro-2-(4-chloro-phenyl)-vinyl)-2,2-dimethyl-cyclopropane-1-carboxylic acid derivatives of the formula (IV) (as defined above) with chlorine or bromine, preferably in the presence of an inert solvent (such as methylene chloride, chlorfrom or carbon tetrachloride) at a temperature between −50° and +50° C., preferably at a temperature between −20° and +30° C.

The halogen is usually employed in a slight excess of up to 30%, preferably between 5 and 20%. After distilling off the solvent and digesting the residue with hydrocarbons, such as, for example hexane, the halogenation product of the formula (II) is obtained in the form of crystals.

Preferred trans-3-(E/Z-2-chloro-2-(4-chloro-phenyl)-vinyl)-2,2-dimethyl-cyclopropane-1-carboxylic acid derivatives of formula (IV) to be used as precursors are those in which R¹ has the meaning given above as preferred.

Examples of the compounds of the formula (IV) which may be mentioned are: trans-3-(E/Z-2-chloro-2-(4-chloro-phenyl)-vinyl)-2,2-dimethyl-cyclopropane-1-carboxylic acid and its chloride, sodium or potassium salt, nitrile, methyl, ethyl, n- or iso-propyl or n-, sec.- or tert.-butyl ester, 3-phenoxybenzyl ester, α-cyano-3-phenoxy-benzyl ester, 4-fluoro-3-phenoxy-benzyl ester of α-cyano-4-fluoro-3-phenoxy-benzyl ester, and trans-3-(E/Z-2-chloro-2-(4-chloro-phenyl)-vinyl-2,2-dimethyl-1-cyclopropyl) methyl ketone.

The compounds of the formula (IV) can be prepared from trans-3-formyl-2,2-dimethyl-cyclopropane-1-carin which R³ represents a hydrogen atom or a cyano group and
R⁴ and R⁵ independently represent a hydrogen or fluorine atom.

Examples of the compounds of the formula (IIIb) which may be mentioned are: trans-3-(1,2,2-trichloro-2(4-chloro-phenyl)-ethyl)-2,2-dimethyl-cyclopropane-1-carboxylic acid 3-phenoxy-benzyl ester, α-cyano-3-phenoxy-benzyl ester, 4-fluoro-3-phenoxy-benzyl ester, 3-(4-fluoro-phenoxy)-benzyl ester, α-cyano-4-fluoro-3-phenoxy-benzyl ester and α-cyano-3-(4-fluoro-phenoxy)-benzyl ester.

The present invention also provides pesticidal composition containing as active ingredient a pesticidally active compound of the present invention in admixture with an inert pesticidal carrier, e.g. a solid or liquefied gaseous diluent or carrier or in admixture with a liquid diluent or carrier containing a surface-active agent.

The present invention also provides a method of combating pests (in particular ectoparasites) which comprises applying to the pests, or to a habitat thereof, a compound of the present invention alone or in the form of a composition containing as active ingredient a pesticidally active compound of the present invention in admixture with an inert diluent or carrier.

The present invention also provides a method of freeing or protecting domesticated animals from parasites which comprises applying to said animals a compound according to the present invention, in admixture with an inert diluent or carrier.

The present invention further provides domesticated animals whenever freed or protected from parasites by the application to said animals of a pesticidally active compound according to the present invention, in admixture with an inert diluent or carrier.

PREPARATIVE EXAMPLES

EXAMPLE 1

Halogenation

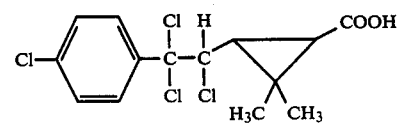

28.5 g (0.1 mole) of trans-3-(E/Z-2-chloro-2-(4-chloro-phenyl)-vinyl-2,2-dimethyl-cyclopropane-1-carboxylic acid with an E:Z ratio of 60:4: were dissolved in 150 ml of carbon tetrachloride, and 8 g (0.113 mole) of chlorine were slowly passed into the reaction mixture at −10° C. whilst stirring. Stirring was then continued for half an hour at 0° C. and then at 20° C. for one and a half hours. Thereafter, the solvent was stripped off in vacuo and the residue was stirred with 100 ml of n-hexane. After cooling the mixture to 0° C., the crystalline solid was filtered off. 32.4 g (91% of theory) of trans-3-(1,2,2-trichloro-2-(4-chloro-phenyl)-ethyl)-2,2-dimethyl-cyclopropane-1-cyclopropane-1-carboxylic acid were obtained as a colourless solid with a melting point of 145°–150° C.

$^1$H—NMR spectrum in CDCl$_3$/TMS, τ (ppm)

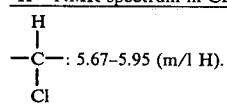
: 5.67–5.95 (m/1 H).

The following compounds were obtained analogously to Example 1:

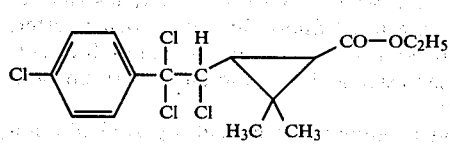
trans
$^1$H—NMR/CDCl$_3$ τ (ppm)

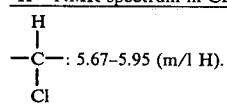
: 5.7–5.95 (m/1 H)

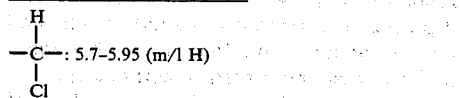

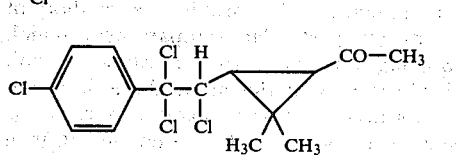
trans
$^1$H—NMR/CDCl$_3$ τ (ppm)

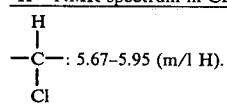
: 5.74–6.05 (m/1 H)

benzyl-H: 3.62–3.85 (m/1 H)

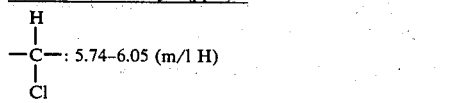

EXAMPLE 2

Dehalogenation:

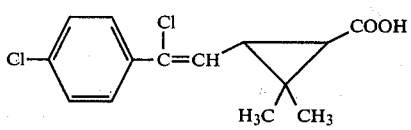

17.8 g (0.05 mole) of trans-3-(1,2,2-trichloro-2-(4-chloro-phenyl)-ethyl)-2,2-dimethyl-cyclopropane-1-carboxylic acid (=halogen compound) were added in portions to a mixture of 100 ml of ethanol and 3.6 g 0.055 mole) of zinc dust (="dehalogenating agent") at 50° C., whilst stirring. The mixture was then heated under reflux for 1 hour, whilst stirring. Thereafter, it was cooled to room temperature and the ethanol was stripped off under a waterpump vacuum. The crystalline residue was taken up in 150 ml of methylene chloride and extracted by shaking, once with 150 ml of water, to which 10 ml of concentrated hydrochloric acid had been added, and then again with 150 ml of water. The organic phase was separated off, dried over magnesium sulphate and freed from the solvent in vacuo. 13.7 g (96% of theory) of trans-3-(Z/E-2-chloro-2-(4-chloro-phenyl)-vinyl)-2,2-dimethyl-cyclopropane-1-carboxylic acid (=end product)were obtained as a Yield:
90% of theory Yield:
85% of theory Yield:
88% of theory Yield:
88% of theory:
melting point: 148° C.

light-yellow solid with a Z:E ratio of 95:5. The Z:E ratio was determined by ¹H-NMR (ratio of the vinyl protons of the Z and E forms).

¹H—NMR in CDCl₃/TMS τ (ppm):

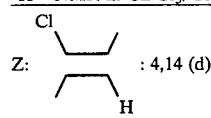
Z: : 4,14 (d)

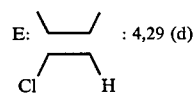
E: : 4,29 (d)

The following compound was obtained analogously to Example 2:

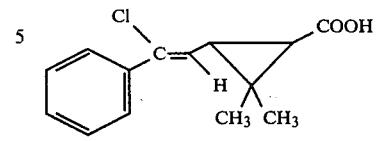

Yield: 95% of theory trans Z (98%)
trans E (2%)

¹H—NMR in CDCl₃/TMS τ (ppm)

| Vinyl-H: | 4.14 (d)/1 H |
| Dimethyl-H: | 8.58 (s)/3 H |
| | 8.74 (s)/3 H |

The E→ Z conversions listed in Table I could be carried out analogously to Examples 1 and 2.

TABLE I (IV)

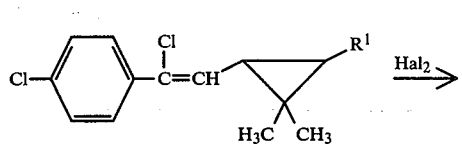

E/Z - 1 RS-trans
Starting material (II)

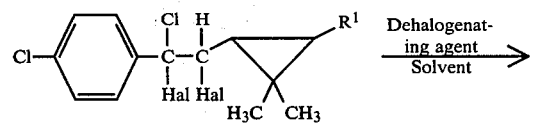

1 RS-trans
Halogen compound (I)

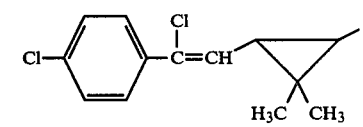

Z/E - 1 RS-trans
End product

| Starting material | % Z | % E | Hal | Dehalogenating agent | Solvent | Temperature Reaction Time |
|---|---|---|---|---|---|---|
| R¹ = —COOH | 40 | 60 | Cl | zinc dust | C₂H₅OH | 80° C. 2 hours |
| R¹ = —COOH | 0 | 100 | Cl | zinc dust | C₂H₅OH | 80° C. 1 hour |
| R¹ = —COOH | 40 | 60 | Cl | zinc dust | dimethyl-formamide | 80–110° C. 2 hours |
| R¹ = —COOH | 40 | 60 | Cl | zinc dust | CH₃COOH | 100° C. 1 hour |
| R¹ = —COOH | 40 | 60 | Br | zinc dust | dimethyl-formamide | 80–110° C. 1 hour |
| R¹ = —COOH | 40 | 60 | Br | zinc dust | C₂H₅OH | 80° C. 1 hour |
| R¹ = —COONa | 40 | 60 | Br | P[N(CH₃)₂]₃ | tetrahydrofuran | 20° C. 2 hours |
| R¹ = —COOH | 40 | 60 | Br | P—(C₆H₅)₃ | toluene | 80° C. 4 hours |

TABLE I-continued

| $R^1 =$ | | | | | | |
|---|---|---|---|---|---|---|
| 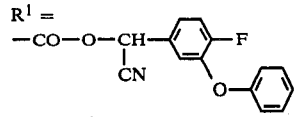 | 40 | 60 | Cl | zinc dust | C₂H₅OH | 80° C. / 1 hour |
| $R^1 = -COOC_2H_5$ | 40 | 60 | Cl | zinc dust | C₂H₅OH | 80° C. / 1.5 hours |
| $R^1 = -COOH$ | 40 | 60 | Br | KI (4 mols) | CH₃OH | 60° C. / 4 hours |
| $R^1 = -COOH$ | 40 | 60 | Br | KI (4 mols) | acetone | 60° C. / 4 hours |
| 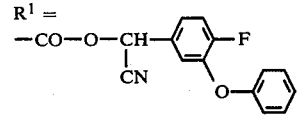 | 40 | 60 | Br | zinc dust | CH₃COOH | 80° C. / 0.5 hour |
| 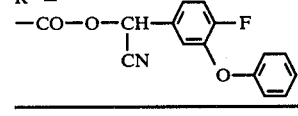 | 40 | 60 | Cl | zinc dust | CH₃COOH | 80° C. / 1 hour |

| End Product | % Z | % E | Yield (% of theory, relative to halogen compounds) |
|---|---|---|---|
| R' = COOH | 95 | 5 | 96 |
| R' = COOH | 94 | 6 | 83 |
| R' = COOH | 96 | 4 | 93 |
| R' = COOH | 97 | 3 | 89 |
| R' = COOH | 79 | 21 | 90.6 |
| R' = COOH | 77 | 23 | 88 |
| R' = COOH | 75 | 25 | 28 |
| R' = COOH | 80 | 20 | 75 |
| 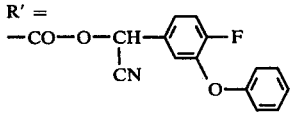 | 96 | 4 | 45 |
| R' = COOC₂H₅ | 96 | 4 | 55 |
| R' = COOH | 70 | 30 | 85 |
| R' = COOH | 70 | 30 | 80 |
| 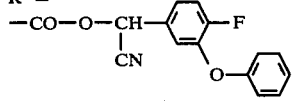 | 85 | 15 | 75 |
| 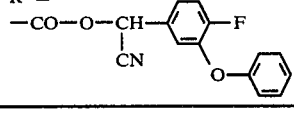 | 97 | 3 | 80 |

EXAMPLE 3

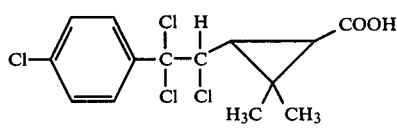

17.7 g (0.05 mole) of trans-3-(E/Z-2-chloro-2-(4-chloro-phenyl)-vinyl)-2,2-dimethyl-1-acetyl-cyclo-propane were dissolved in 50 ml of carbon tetrachloride, and 8 g of chlorine were slowly passed into the reaction mixture at −15° C. whilst stirring. Stirring was then continued for half an hour at 0° C. and then at 20 ° C. for 1½ hours. Thereafter, the solvent was stripped off in vacuo. The viscous oily residue was dissolved in 25 ml of tetrahydrofuran and the solution was slowly added dropwise to a mixture of 17.9 g of sodium hydroxide, 90 ml of water and 21.4 g of bromine at 30°–35° C., whilst stirring. The mixture was then stirred at room temperature for 2 hours. The tetrahydrofuran was subsequently distilled off in vacuo, and 200 ml of water were added to the residue. The aqueous phase was extracted twice by shaking with 100 ml of methylene chloride. The aqueous phase was then acidified with concentrated hydrochloric acid and the oil which had precipitated was extracted twice with 150 ml of methylene chloride. The combined methylene chloride phases were dried over magnesium sulphate and the solvent was then distilled off in vacuo. 9.6 g (53.9% of theory) of trans-3-(1,2,2-trichloro-2-(4-chloro-phenyl)-ethyl)-2,2-dimethyl-cyclopropanecarboxylic acid were obtained as a viscous oil. The structure was confirmed by the ¹HNMR spectrum.

EXAMPLE 4

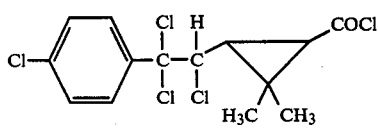
(a)

14 g of trans-3-(1,2,2-trichloro-2-(4-chloro-phenyl)-ethyl)-2,2-dimethyl-cyclopropane-1-carboxylic acid were dissolved in 100 ml of carbon tetrachloride, 75 g of thionyl chloride were added and the mixture was heated under reflux for 4 hours. The solvent and excess thionyl chloride were then stripped off in vacuo. 13.7 g of trans-3-(1,2,2-trichloro-2-(4-chloro-phenyl)-ethyl)-2,2-dimethyl-cyclopropane-1-carboxylic acid chloride were obtained as a viscous oil.

The following compound was obtained analogously to Example 4:

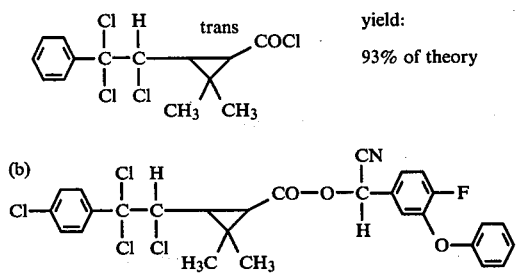

yield: 93% of theory 6.36 g (0.017 mole) of trans-3-(1,2,2-trichloro-2-(4-chloro-phenyl)-ethyl)-2,2-dimethyl-cyclo-propane-1-carboxylic acid chloride and 3,67 g (0.017 mole) of 3-phenoxy-4-fluoro-benzaldehyde were together added dropwise to a mixture of 1.13 g of sodium cyanide, 1.7 ml of water, 100 ml of n-hexane and 0.6 g of tetrabutylammonium bromide at 20°-25° C., whilst stirring, and the mixture was then stirred at 20°-25° C. for 4 hours. 300 ml of toluene were subsequently added to the reaction mixture, and the mixture was extracted twice by shaking with 300 ml of water each time. The organic phase was separated off and dried over magnesium sulphate, and the solvent was distilled off under a waterpump vacuum. Last residues of solvent were removed by brief incipient distillation at a bath temperature of 60° C./1 mm Hg. 8.5 g (86% of theory) of trans-3-(1,2,2-trichloro-2-(4-chloro-phenyl)-ethyl)-2,2-dimethyl-cyclopropane-1-carboxylic acid α-cyano-3-phenoxy-4-fluorobenzyl ester were obtained as a viscous oil.

¹H—NMR in CDCl₃/TMS τ (ppm):

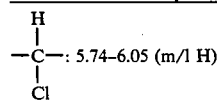: 5.74–6.05 (m/1 H)

benzyl-H: 3.62–3.85 (m/1 H)

The following compound was obtained analogously:

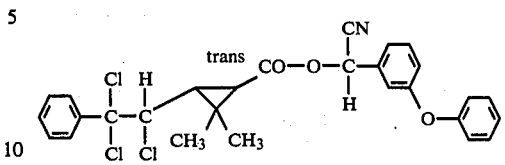

Yield: 87% of theory

¹H—NMR in CDCl₃/TMS, τ (ppm):

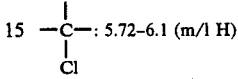: 5.72–6.1 (m/1 H)

benzyl-H: 3.64–3.83 (m/1 H)

The pesticidal activity of the compounds of this invention is illustrated by the following biotest Examples.

EXAMPLE A

Test with *Psoroptes cuniculi*
Solvent:
    35 parts by weight of ethylene glycol monoether ether
    35 parts by weight of nonylphenol polyglycol ether To produce a suitable preparation of active compound, three parts by weight of active compound were mixed with seven parts by weight of the solvent indicated above, and the concentrate thus obtained was diluted with water to the desired concentration.

About 10 –25 *Psoroptes cuniculi* were introduced into 1 ml of the active compound preparation to be tested, which had been pipetted into tablet nests of a deep-drawn pack. After 24 hours, the degree of destruction was determined.

In this test, the compounds, according to the invention, of the preparation examples showed a superior action compared to the prior art.

EXAMPLE B

Test with *Boophilus microplus* resistant
Solvent:
    35 parts by weight of ethylene glycol momoethyl ether
    35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult *Boophilus microplus* res. were immersed for 1 minute in the active compound preparation to be tested. After transfer to plastic beakers and storage in a climatically controlled chamber, the degree of destruction was determined.

In this test, the compounds, according to the invention, of the preparation examples showed a superior action compared to the prior art.

EXAMPLE C

Test with *Lucilia cuprina* res. larvae
Emulsifier:
    35 parts by weight of ethylene glycol momoethyl ether
    35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

About 20 *Lucilia cuprina* res. larvae were introduced into a test tube which contained approx 1 cm² of horse muscle and 0.5 ml of the preparation of active compound. After 24 hours, the degree of destruction was determined.

In this test, the compounds, according to the invention, of the preparation examples showed a superior action compared to the prior art.

What is claimed is:

1. A process for the preparation of a trans-3-(Z-2-chloro-2-aryl-vinyl)-2,2-dimethyl-cyclopropane-1-carboxylic acid derivative of the formula

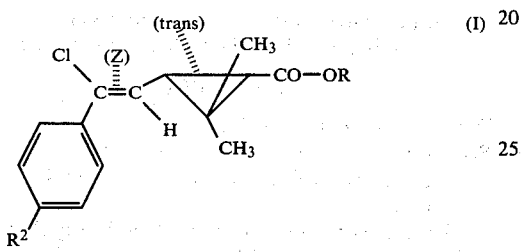

in which
R² represents a hydrogen or chlorine atom, and
R represents a hydrogen atom, an alkali metal or one equivalent of an alkaline earth metal, an optionally substituted ammonium ion, an alkyl radical, or a phenoxybenzyl radical which is optionally substituted by alkyl, alkenyl, alkinyl, halogen and/or cyano, which comprises reacting 1 to 2 moles of a trans-3-(1,2-dihalogen-2-chloro-2-aryl-ethyl)-2,2-dimethyl-cyclopropanel-1-carboxylic acid derivatives of the formula

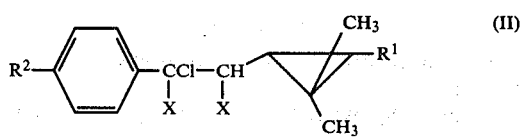

in which

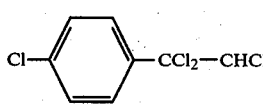

R² represents a hydrogen or chlorine atom,
R¹ represents a cyano, acetyl, chlorocarbonyl or a —COOR radical,
wherein
R has the abovementioned meaning, and
X represents a chlorine or bromine atom,
per mol dehalogenating agent suitable for the elimination of two vicinal halogen atoms, at a temperature between 0° and 150° C. and if R¹ in the compound of formula (II) does not denote the —COOR radical, the product of the formula

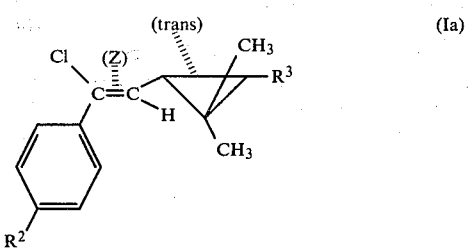

in which
R² represents hydrogen or chlorine and
R³ represents cyano, acetyl or chlorocarbonyl, is converted into a compound of the formula (I).

2. A process according to claim 1, characterised in that the reaction with the dehalogenating agent is carried out in the presence of a diluent.

3. A process according to claim 1 or 2, characterised in that the dehalogenating agent is zinc.

4. A process according to claims 1 or 2, characterised in that the reaction is carried out at a temperature between 20° and 120° C.

5. A process according to claims 1 or 2, characterised in that 1 to 1.5 moles of dehalogenating agents are used per mole of starting compound of formula (II).

6. A trans-3-(1,2,2-Trichloro-2-(4-chloro-phenyl)-ethyl)-2,2-dimethyl-cyclopropane-1-carboxylic acid derivative of the formula

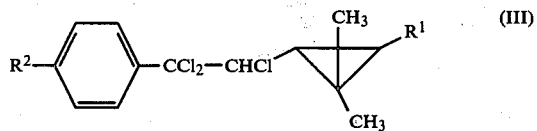

in which
R² represents a hydrogen or chlorine atom and
R¹ has the same meaning as in claim 1.

7. A compound according to claim 6, in which
R² represents a hydrogen or chlorine atom, and
R¹ represents a phenoxybenzyloxycarbonyl radical which is optionally substituted by alkyl, alkenyl, alkinyl, halogen and/or cyano.

8. A compound according to claim 6, of the general formula

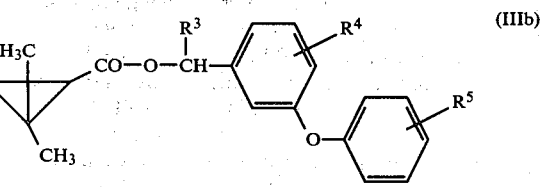

in which
R³ denotes a hydrogen atom or a cyano group, and
R⁴ and R⁵ independently denote a hydrogen or fluorine atom.

9. A process for the production of a compound of claim 6, which comprises reacting 1 to 2 mol of a trans-3-(E/Z-2-chloro-2-(4-aryl)-vinyl)-2,2-dimethyl-cyclopropanel-1-carboxylic acid derivative of the formula

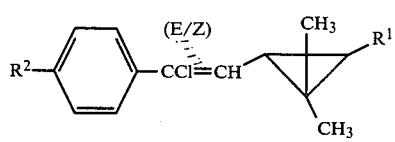 (IV)

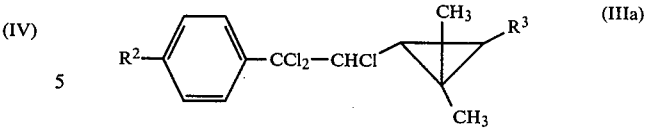 (IIIa)

in which R[1] represents a cyano, acetyl, chlorocarbonyl or —COOR radical wherein R represents R[2] represents a hydrogen or chlorine atom, and R represents a hydrogen atom, an alkali metal or one equivalent of an alkaline earth metal, an optionally substituted ammonium ion, an alkyl radical, or a phenoxybenzyl radical which is optionally substituted by alkyl, alkenyl, alkinyl, halogen and/or cyano, and R' represents a hydrogen or chlorine atom, with chlorine at a temperature between −50° and +50° C. and, if R[1] in the compound of formula (IV) is other than the —COOR radical, the product of the formula in which
R[2] represents a hydrogen or chlorine atom and
R[3] represents a cyano, acetyl or chlorocarbonyl radical, 10. A process according to claim 9, when carried out in the presence of a diluent.

11. A pesticidal composition, comprising as active ingredient a compound according to claims 9 or 10 in admixture with an inert pesticidal carrier.

12. A method of combating pests, which comprises applying to the said pests, or to a habitat thereof, an active compound according to claims 9 or 10 alone or in the form of a composition containing said active compound in admixture with an inert pesticidal carrier.

13. A method of freeing or protecting a domesticated animal from parasites, which comprises applying to said animal a compound according to claims 9 or 10, in admixture with an inert pesticidal carrier.

* * * * *